US009133452B2

(12) United States Patent
Ueda et al.

(10) Patent No.: US 9,133,452 B2
(45) Date of Patent: Sep. 15, 2015

(54) HIGH-SPEED MATURATION METHOD FOR AN OLIGONUCLEOTIDE LIBRARY FOR THE PURPOSE OF PREPARING A PROTEIN LIBRARY

(75) Inventors: Takuya Ueda, Tokyo (JP); Takashi Kanamori, Chiba (JP); Kanehisa Kojoh, Chiba (JP); Shizue Katoh, Chiba (JP); Akira Miyakoshi, Chiba (JP)

(73) Assignees: The University of Tokyo, Tokyo (JP); GeneFrontier Corporation, Kashiwa (JP)

( * ) Notice: Subject to any disclaimer, the term of this patent is extended or adjusted under 35 U.S.C. 154(b) by 0 days.

(21) Appl. No.: 13/806,470

(22) PCT Filed: Jun. 23, 2011

(86) PCT No.: PCT/JP2011/064455
§ 371 (c)(1),
(2), (4) Date: Feb. 7, 2013

(87) PCT Pub. No.: WO2001/162355
PCT Pub. Date: Dec. 29, 2011

(65) Prior Publication Data
US 2013/0143773 A1    Jun. 6, 2013

(30) Foreign Application Priority Data
Jun. 23, 2010  (JP) ................................. 2010-142470

(51) Int. Cl.
*C12N 15/10* (2006.01)
*C12N 15/67* (2006.01)

(52) U.S. Cl.
CPC ........ *C12N 15/1065* (2013.01); *C12N 15/1093* (2013.01); *C12N 15/67* (2013.01)

(58) Field of Classification Search
CPC . C12N 15/1065; C12N 15/67; C12N 15/1093
USPC ..................................... 506/26, 23
See application file for complete search history.

(56) References Cited

U.S. PATENT DOCUMENTS

2009/0104663 A1*   4/2009   Subkowski et al. .......... 435/69.7

FOREIGN PATENT DOCUMENTS

| JP | 2007/029061 A |   | 2/2007 |
| JP | 2007029061 A | * | 2/2007 |

(Continued)

OTHER PUBLICATIONS

Larsson et al., Nucleic Acids Research, 2002, 30(23), pp. 1-8.*

(Continued)

*Primary Examiner* — Larry Riggs
*Assistant Examiner* — Karla Dines
(74) *Attorney, Agent, or Firm* — Leydig, Voit & Mayer, Ltd.

(57) ABSTRACT

The present invention provides a method of producing a maturated oligonucleotide library, including a step of obtaining a terminal-modified product of a maturation target oligonucleotide library, including adding a tag sequence to the 5' terminus of the maturation target oligonucleotide library and an arrest sequence, which stalls translation elongation on a ribosome, to the 3' terminus of the maturation target oligonucleotide library, a step of transcribing the terminal-modified sequence product to give a transcript, and a step of in vitro translation for translating the transcript in vitro, wherein the maturation target oligonucleotide library is a random oligonucleotide library.

10 Claims, 1 Drawing Sheet

Before maturation

SEQ ID NO: 9 : CGCTTGCTGGTGCGCATCGAGTTGTAC
SEQ ID NO: 10: GTCTAGGTCTCCCTCCGCTGGCTCGGG
SEQ ID NO: 11: TAGGTCTAGACGATGGTGTACTGCCTC
SEQ ID NO: 12: TTCTGGGTCCCGGTGCTCTTGACGTTG
SEQ ID NO: 13: TAGTCCTTCTTGTGCATCTCGGGCTGC
SEQ ID NO: 14: AGGCTGGTGTTCTTCCGCCGGAGGTTG
SEQ ID NO: 15: TTCTCCGTGAAGTGCGTGCACTAGATC
SEQ ID NO: 16: TTGTTGTTGATGATCAGGACGTTCAGC
SEQ ID NO: 17: GACTGCTCGTGGAAGTTGAAGGTGTGC
SEQ ID NO: 18: GTCATCTCCGACTTGGCCCACGGCATG
SEQ ID NO: 19: GGGCTGGTGGTGTCCTGCATCGTGGTC
SEQ ID NO: 20: TAGTACGGGTTGTACATGTGCGCGACC
SEQ ID NO: 21: TGGGCGGTGTTCTAGCGCGTCATCTTG
SEQ ID NO: 22: CGGATGTAGATGTAGATGTCCATGTGG
SEQ ID NO: 23: TTCACCTTGCAGGTCATGTCCGTCGTC
SEQ ID NO: 24: TTGTTGTTGTTCAGGTGGCGCTACTTC
SEQ ID NO: 25: GCGGAGTTGAGCCGGCAGCCCCGCAC_
SEQ ID NO: 26: GGCGGCTGCTCGGGGAGGCAGTTGTTG
SEQ ID NO: 27: GTCAGGAACCAGCCCCTCGGCATGAAC
SEQ ID NO: 28: CTCTGCTTGTGGTCGTAGATGACGGAC

After maturation

SEQ ID NO: 29: TTCTTCATGGTCTCCAACGTCTCGATC
SEQ ID NO: 30: GACAAGAGGTGGCAGCTGCACTCGCCC
SEQ ID NO: 31: GGGAGCCCCTGGGAGTGGTACAACCTG
SEQ ID NO: 32: CTCCGAGTGTTCTTCTTGGCGATCTAC
SEQ ID NO: 33: CGCAACCTCTTGACCTGGGACTACCTC
SEQ ID NO: 34: TCCTCCGTCTTCGGCTTCTTCGTGTGC
SEQ ID NO: 35: TTCCTCATCCGCCTCAGCCTGCGCAAC
SEQ ID NO: 36: TCCCTCCTCAGCATGTGCTTGTGCATC
SEQ ID NO: 37: TGGCCGTTCGTCGTGGGCGTGCTGGAC
SEQ ID NO: 38: TTCGTCTTCCACCTCTGCCAATACTAC
SEQ ID NO: 39: CTCCGAGTGTTCTTCTCGGCGTGCATC
SEQ ID NO: 40: TGGACGCCGCCCCAGGCCATCTCGATC
SEQ ID NO: 41: GGGGGCCTCTTGTTGTGGATGCACGCG
SEQ ID NO: 42: TCCGCGAACGACCGCTTGTTGGCCACC
SEQ ID NO: 43: TTGAGGTCCTTGGCCCCGTGGCGCTTC
SEQ ID NO: 44: GAGTGCCGGGCGGCGCTGGGCCCGAAC
SEQ ID NO: 45: TCCAAGACCGAGTTGCTGTGGGCCTCC
SEQ ID NO: 46: GGCGGGAGCTTCGGGCCGTCGCCCCGC
SEQ ID NO: 47: AGGTTCAGCGGGTTCGAGCCCATGTTG
SEQ ID NO: 48: TTCTCGAGGCAGCTGATGATGGCTTGG

(56) References Cited

FOREIGN PATENT DOCUMENTS

| JP | 2008/271903 A | | 11/2008 |
|----|---------------|---|---------|
| JP | 2009/112286 A | | 5/2009 |
| JP | 2009112286 A | * | 5/2009 |
| WO | 2012/074029 A | | 6/2012 |

OTHER PUBLICATIONS

Ohashi et al., Biochemical and Biophysical Research Communications, Jan. 2007, 352(1), pp. 270-276.*
Einhauer et al., J. Bioechem. Biophys. Methods, 2001, 49 pp. 455-465.*
Cho et al., *Journal of Molecular Biology*, 297: 309-319 (2000).
Gong et al., *Science*, 297: 1864-1867 (2002).
Hanes et al., *Proc. Natl. Acad. Sci. USA*, 94: 4937-4942 (2007).
Hood et al., *Annual Review of Microbiology*, 63: 385-409 (2009).
Kanamori et al., "Development of cell-free protein synthesis system suitable for ribosome display," *The 11th Annual Meeting of the Protein Science Society of Japan*, Osaka, Japan (Jun. 7-9, 2011).
Kojoh et al., Poster presentation, "In vitro affinity maturation based on Ribosome Display System with PUREfrex," *Protein and Antibody Engineering Summit*, Boston, MA (Apr. 30, 2012-May 4, 2012).
Kojoh et al., Poster presentation, "In vitro affinity maturation based on Ribosome Display System with PUREfrex," *The 35th Annual Meeting of the Molecular Biology Society of Japan*, Fukuoka, Japan (Dec. 11-14, 2012).
Kojoh et al., Poster presentation, "In vitro selection from designed protein scaffold library with Ribosome Display on PURE system," *Protein and Antibody Engineering Summit*, Boston, MA (May 9-13, 2011).
Kojoh et al., Poster presentation, "In vitro selection from designed protein scaffold library with Ribosome Display on PURE system", *The 34th Annual Meeting of the Molecular Biology Society of Japan*, Yokohama, Japan (Dec. 13-16, 2011).
Moore et al., *Annual Review of Biochemistry*, 76: 101-124 (2007).
Nakatogawa et al., *Cell*, 108: 629-636 (2002).
Ohashi et al., *Biochem. Biophys. Res. Commun.*, 352: 270-276 (2007).
Osada et al., *The Journal of Biochemistry*, 145(5): 693-700 (2009).
Shimizu et al., *Methods*, 36: 299-304 (2005).
Shimizu et al., *Nature Biotechnology*, 19: 751-755 (2001).
Tanner et al., *The Journal of Biological Chemistry*, 284: 34809-34818 (2009).
Villemagne et al., *Journal of Immunological Methods*, 313: 140-148 (2006).
Japanese Patent Office, International Search Report in International Patent Application No. PCT/JP2011/064455 (Aug. 2, 2011).
International Bureau of WIPO, International Preliminary Report on Patentability in International Patent Application No. PCT/JP2011/064455 (Jan. 15, 2013).

* cited by examiner

SEQUENCE LISTING

```
<160> NUMBER OF SEQ ID NOS: 48

<210> SEQ ID NO 1
<211> LENGTH: 84
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(84)
<223> OTHER INFORMATION: n stands for any base.
      s stands for guanine or cytosine.
```

<400> SEQUENCE: 1
atggactata aagatgacga tgacaaanns nnsnnsnnsn nsnnsnnsnn snnsgagcag    60
aagctgatct ctgaggagga tctg    84

<210> SEQ ID NO 2
<211> LENGTH: 112
<212> TYPE: DNA
<213> ORGANISM: Artificial Sequence
<220> FEATURE:
<223> OTHER INFORMATION: Synthetic oligonucleotide comprising T7
      promoter, SD sequence and start codon

<400> SEQUENCE: 2
gaaattaata cgactcacta gggagacc acaacggttt ccctctagaa ataattttgt    60
ttaactttaa gaaggagata taccaatgga ctataaagat gacgatgaca aa    112

<210> SEQ ID NO 3
<211> LENGTH: 54
<212> TYPE: DNA
<213> ORGANISM: Artificial Sequence
<220> FEATURE:
<223> OTHER INFORMATION: Synthetic primer

<400> SEQUENCE: 3
gagcagaagc tgatctctga ggaggatctg gaatatcaag gccaatcgtc tgac    54

<210> SEQ ID NO 4
<211> LENGTH: 108
<212> TYPE: DNA
<213> ORGANISM: Artificial Sequence
<220> FEATURE:
<223> OTHER INFORMATION: Synthetic primer

<400> SEQUENCE: 4
ctcgagttat tcattaggtg aggcgttgag ggccagcacg gatgccttgc gcctggctta    60
tccagacggg cgtgctgaat tttgcgccgg aaacgtcacc aatgaaac    108

<210> SEQ ID NO 5
<211> LENGTH: 48
<212> TYPE: DNA
<213> ORGANISM: Artificial Sequence
<220> FEATURE:
<223> OTHER INFORMATION: Synthetic primer

<400> SEQUENCE: 5
gaaattaata cgactcacta gggagacc acaacggttt ccctctag    48

<210> SEQ ID NO 6
<211> LENGTH: 32
<212> TYPE: DNA
<213> ORGANISM: Artificial Sequence
<220> FEATURE:
<223> OTHER INFORMATION: Synthetic primer

<400> SEQUENCE: 6
ggattagtta ttcattaggt gaggcgttga gg    32

<210> SEQ ID NO 7
<211> LENGTH: 22
<212> TYPE: DNA
<213> ORGANISM: Artificial Sequence
<220> FEATURE:
<223> OTHER INFORMATION: Synthetic primer

<400> SEQUENCE: 7
cagatcctcc tcagagatca gc				22

<210> SEQ ID NO 8
<211> LENGTH: 27
<212> TYPE: DNA
<213> ORGANISM: Artificial Sequence
<220> FEATURE:
<223> OTHER INFORMATION: Synthetic primer

<400> SEQUENCE: 8
atggactata aagatgacga tgacaaa				27

<210> SEQ ID NO 9
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 9
cgcttgctgg tgcgcatcga gttgtac				27

<210> SEQ ID NO 10
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 10
gtctaggtct ccctccgctg gctcggg				27

<210> SEQ ID NO 11
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 11
taggtctaga cgatggtgta ctgcctc				27

<210> SEQ ID NO 12
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 12
ttctgggtcc cggtgctctt gacgttg				27

<210> SEQ ID NO 13
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 13
tagtccttct tgtgcatctc gggctgc                                    27

<210> SEQ ID NO 14
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 14
aggctggtgt tcttccgccg gaggttg                                    27

<210> SEQ ID NO 15
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 15
ttctccgtga agtgcgtgca ctagatc                                    27

<210> SEQ ID NO 16
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 16
ttgttgttga tgatcaggac gttcagc                                    27

<210> SEQ ID NO 17
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 17
gactgctcgt ggaagttgaa ggtgtgc                                    27

<210> SEQ ID NO 18
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 18
gtcatctccg acttggccca cggcatg                                    27

<210> SEQ ID NO 19
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 19

```
gggctggtgg tgtcctgcat cgtggtc                                              27
```

<210> SEQ ID NO 20
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 20

```
tagtacgggt tgtacatgtg cgcgacc                                              27
```

<210> SEQ ID NO 21
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 21

```
tgggcggtgt tctagcgcgt catcttg                                              27
```

<210> SEQ ID NO 22
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 22

```
cggatgtaga tgtagatgtc catgtgg                                              27
```

<210> SEQ ID NO 23
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 23

```
ttcaccttgc aggtcatgtc cgtcgtc                                              27
```

<210> SEQ ID NO 24
<211> LENGTH: 27
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 24

```
ttgttgttgt tcaggtggcg ctacttc                                              27
```

<210> SEQ ID NO 25
<211> LENGTH: 26
<212> TYPE: DNA
<213> ORGANISM: Artificial Sequence
<220> FEATURE:
<223> OTHER INFORMATION: Synthetic Synthetic oligonucleotide before
      maturation

<400> SEQUENCE: 25

```
gcggagttga gccggcagcc ccgcac                                               26
```

<210> SEQ ID NO 26
<211> LENGTH: 27
<212> TYPE: DNA
<213> ORGANISM: Artificial Sequence
<220> FEATURE:
<223> OTHER INFORMATION: Synthetic Synthetic oligonucleotide before maturation

<400> SEQUENCE: 26
ggcggctgct cggggaggca gttgttg                                  27

<210> SEQ ID NO 27
<211> LENGTH: 27
<212> TYPE: DNA
<213> ORGANISM: Artificial Sequence
<220> FEATURE:
<223> OTHER INFORMATION: Synthetic Synthetic oligonucleotide before maturation

<400> SEQUENCE: 27
gtcaggaacc agcccctcgg catgaac                                  27

<210> SEQ ID NO 28
<211> LENGTH: 27
<212> TYPE: DNA
<213> ORGANISM: Artificial Sequence
<220> FEATURE:
<223> OTHER INFORMATION: Synthetic Synthetic oligonucleotide before maturation

<400> SEQUENCE: 28
ctctgcttgt ggtcgtagat gacggac                                  27

<210> SEQ ID NO 29
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 29
ttcttcatgg tctccaacgt ctcgatc                                  27

<210> SEQ ID NO 30
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 30
gacaagaggt ggcagctgca ctcgccc                                  27

<210> SEQ ID NO 31
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 31
gggagcccct gggagtggta caacctg                                  27

<210> SEQ ID NO 32
<211> LENGTH: 27

-continued

```
<212> TYPE: DNA
<213> ORGANISM: Artificial Sequence
<220> FEATURE:
<223> OTHER INFORMATION: oligonucleotide after maturation

<400> SEQUENCE: 32
ctccgagtgt tcttcttggc gatctac                                          27

<210> SEQ ID NO 33
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 33
cgcaacctct tgacctggga ctacctc                                          27

<210> SEQ ID NO 34
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 34
tcctccgtct tcggcttctt cgtgtgc                                          27

<210> SEQ ID NO 35
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 35
ttcctcatcc gcctcagcct gcgcaac                                          27

<210> SEQ ID NO 36
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 36
tccctcctca gcatgtgctt gtgcatc                                          27

<210> SEQ ID NO 37
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 37
tggccgttcg tcgtgggcgt gctggac                                          27

<210> SEQ ID NO 38
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 38
```
ttcgtcttcc acctctgcca atactac                          27

<210> SEQ ID NO 39
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 39
ctccgagtgt tcttctcggc gtgcatc                          27

<210> SEQ ID NO 40
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 40
tggacgccgc cccaggccat ctcgatc                          27

<210> SEQ ID NO 41
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 41
gggggcctct tgttgtggat gcacgcg                          27

<210> SEQ ID NO 42
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 42
tccgcgaacg accgcttgtt ggccacc                          27

<210> SEQ ID NO 43
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 43
ttgaggtcct tggccccgtg gcgcttc                          27

<210> SEQ ID NO 44
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 44
gagtgccggg cggcgctggg cccgaac                          27

<210> SEQ ID NO 45
<211> LENGTH: 27
<212> TYPE: DNA
<213> ORGANISM: Artificial Sequence

```
<220> FEATURE:
<223> OTHER INFORMATION: oligonucleotide after maturation

<400> SEQUENCE: 45
tccaagaccg agttgctgtg ggcctcc                                              27

<210> SEQ ID NO 46
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 46
ggcgggagct tcgggccgtc gccccgc                                              27

<210> SEQ ID NO 47
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 47
aggttcagcg ggttcgagcc catgttg                                              27

<210> SEQ ID NO 48
<211> LENGTH: 27
<212> TYPE: DNA
<213> ORGANISM: Artificial Sequence
<220> FEATURE:
<223> OTHER INFORMATION: oligonucleotide after maturation

<400> SEQUENCE: 48
ttctcgaggc agctgatgat ggcttgg                                              27
```

HIGH-SPEED MATURATION METHOD FOR AN OLIGONUCLEOTIDE LIBRARY FOR THE PURPOSE OF PREPARING A PROTEIN LIBRARY

CROSS-REFERENCE TO RELATED APPLICATIONS

This patent application is the U.S. national phase of International Patent Application No. PCT/JP2011/064455, filed on Jun. 23, 2011, which claims the benefit of Japanese Patent Application No. 2010-142470, filed on Jun. 23, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 10,836 bytes ASCII (Text) file named "711953ReplacementSequenceListing-2nd.txt," created Sep. 27, 2013.

TECHNICAL FIELD

The present invention relates to a fast maturation method of an oligonucleotide library, which aims to prepare a protein library.

BACKGROUND ART

When plural random amino acid sequences are introduced into one site of a protein, oligonucleotides synthesized at random are introduced into the gene of the protein. However, when an introduced sequence is synthesized completely at random (NNN sequence), a stop codon emerges at a ratio of about 1/21. In addition, when synthesized an oligonucleotide to be introduced is a long strand, an oligonucleotide having deleted or inserted bases is found in a proportion of a few percent. Since they markedly reduce the diversity of the resulting protein library, those oligonucleotides need to be removed during preparation of the oligonucleotide library.

As a method for removing such unnecessary oligonucleotides from a synthesized oligonucleotide library, a method utilizing antibiotic drug selection can be mentioned. For example, a random oligonucleotide library to be the maturation target is ligated to the 5' terminus of a drug resistance gene such as β-lactamase, and introduced into a plasmid. *Escherichia coli* is transformed with this plasmid and applied to an agar plate containing the corresponding antibiotic. As a result, only *Escherichia coli* having an in-frame gene without a stop codon or a frame shift due to deletion or insertion of bases can grow as a colony on the plate, since such *Escherichia coli* can express a drug resistance protein. Therefore, by recovering a gene from such colonies, a maturated oligonucleotide library free of unnecessary oligonucleotides can be obtained.

However, this method has some problems. Firstly, it is difficult to form a large number of colonies by a general method, since the number of colonies of *Escherichia coli* varies depending on the ligation efficiency of oligonucleotide library to a vector and transformation efficiency of *Escherichia coli*. Secondly, to obtain a large number of colonies, the corresponding number of samples needs to be prepared, which requires a lot of efforts and time.

The period that the present inventors required to maturate an oligonucleotide library having $10^8$ diversities by this method was about 1 week. When an oligonucleotide library encoding an antibody gene library wherein 6 CDRs (complementary-determining regions) of the antibody are randomized is prepared, oligonucleotide libraries encoding each of these 6 CDRs are sequentially maturated, and maturation of the whole oligonucleotide library encoding the antibody gene library requires about 6 weeks.

Furthermore, since the above-mentioned manipulation requires large amounts of expensive reagents (enzymes etc.), the method is extremely costly.

On the other hand, patent document 1 discloses a ribosome display. In addition, patent document 1, paragraph [0051], discloses mRNA having a sequence encoding a translation reaction elongation arrest sequence of *Escherichia coli* SecM at the downstream of a spacer sequence.

DOCUMENT LIST

Patent Document patent document 1: JP-A-2008-271903

SUMMARY OF THE INVENTION

Problems to be Solved by the Invention

The present invention aims to provide a production method of a maturated oligonucleotide library, which can conveniently produce many kinds of maturated oligonucleotide libraries at once in a short time at a low cost.

In addition, the present invention aims to provide an efficient maturation method of a random oligonucleotide library using a ribosome display of an in vitro selection system (JP-A-2008-271903).

Means of Solving the Problems

The present invention is based on the finding that, in maturation of a random oligonucleotide library, the in-frame ratio can be improved by adding an arrest sequence (e.g., SecM sequence) to the 3' terminus of oligonucleotide, and maturation can be achieved extremely efficiently.

The first aspect of the present invention relates to a production method of a maturated oligonucleotide library. In this method, first, a tag sequence is added to the 5' terminus of a maturation target oligonucleotide library and an arrest sequence (e.g., SecM sequence) is added to the 3' terminus thereof to give a terminal-modified product of a maturation target oligonucleotide library (terminal-modified sequence product). The maturation target oligonucleotide library is a random oligonucleotide library. Examples of the random oligonucleotide library include an oligonucleotide library containing an NNS sequence. Examples of the NNS sequence include an NNS sequence containing a codon corresponding to 31 amino acids. When the maturation target oligonucleotide library is a completely random oligonucleotide library, a stop codon emerges at a rate of about 1/21. Therefore, the random oligonucleotide library is preferably free of a completely random sequence (NNN).

Then, a transcript of the terminal-modified sequence product is obtained by transcription thereof. Thereafter, the transcript is translated in vitro.

In the above-mentioned method, the tag sequence is exemplified by FLAG sequences. For example, the resultant product can be easily recovered by using beads on which an anti-FLAG antibody is immobilized.

In the above-mentioned method, it is preferable to translate a transcript in vitro by using a cell-free translation system. Since the treatment is completely performed in vitro, the maturation efficiency of the oligonucleotide library can be improved. Examples of the cell-free translation system include an *Escherichia coli* cell-free translation system. Preferred as a cell-free translation system is a reconstituted cell-free translation system, i.e., PURE system. A reconstituted cell-free protein synthesis system that has been developed by a group including the present inventor is a synthesis system consisting exclusively of specified factors involved in protein synthesis reaction, such as translation factors and ribosome.

Ribosome display is a method that includes forming an mRNA-ribosome-oligopeptide ternary complex (ribosome display complex) in in vitro translation system and selecting a protein encoding a polypeptide having a specific function. As mentioned above, the terminal-modified product of the present invention has an arrest sequence at the 3' terminus of the maturation target oligonucleotide library. When an oligonucleotide constituting a random oligonucleotide library introduced into an in vitro translation system contains a stop codon, or when a frame shift exists due to the deletion or insertion of bases, normal translation up to the arrest sequence is not available during translation. Thus, translation of an oligonucleotide having a stop codon introduced therein or an oligonucleotide containing a frame shift fails to form a ternary complex of mRNA-ribosome-oligopeptide. Thus, only an in-frame oligonucleotide translated up to the arrest sequence can be selected by, for example, selecting such complex with an antibody to the introduced tag sequence.

Effect of the Invention

In the production method of the maturated oligonucleotide library of the present invention, the treatment is performed completely in vitro, and therefore, an oligonucleotide library having high diversity (e.g., not less than $10^{11}$-$10^{12}$ diversities) can be the target of selection.

The production method of a maturated oligonucleotide library of the present invention includes convenient and efficient operations, and therefore, for example, 8 kinds of maturation target oligonucleotide libraries individually formed can be simultaneously maturated in one day. This is a remarkable difference from conventional methods that require about 1 week for maturation of one kind of oligonucleotide library.

Furthermore, the production method of a maturated oligonucleotide library of the present invention can simultaneously achieve reduction of cost, since it does not require a large amount of expensive enzymes.

DESCRIPTION OF EMBODIMENTS

Figure 1:
FIG. 1 shows a random oligonucleotide library (NNS sequence) before and after maturation.

The first aspect of the present invention relates to a production method of a maturated oligonucleotide library. In this method, first, a tag sequence is added to the 5' terminus of a maturation target oligonucleotide library and an arrest sequence (e.g., SecM sequence) is added to the 3' terminus thereof to give a terminal-modified sequence product of a maturation target oligonucleotide library.

In the present specification, "maturation" refers to removing oligonucleotides containing a stop codon and a frame shift due to the deletion or insertion of bases from an oligonucleotide library. The "maturation target oligonucleotide library" means a mixture of oligonucleotides that can be maturated. The "random oligonucleotide library" means a mixture of oligonucleotides having various sequences as defined below. The "maturated oligonucleotide library" means a mixture of maturated oligonucleotides.

The maturation target oligonucleotide library is exemplified by a random oligonucleotide library. The random oligonucleotide library is exemplified by an oligonucleotide library containing an NNS sequence. NNS sequence is exemplified by an NNS sequence containing 31 amino acid codons. When the maturation target oligonucleotide library is a completely random oligonucleotide library, a stop codon emerges at a ratio of about 1/21. Therefore, a random oligonucleotide library is preferably free of a completely random sequence (NNN). Such random sequence (incomplete random sequence) is exemplified by NNK sequence, NNS sequence and NNY sequence. Here, N means any of adenine (A), guanine (G), cytosine (C) and thymine (T). K means any of guanine (G) and thymine (T). S means any of cytosine (C) and guanine (G). Y means any of cytosine (C) and thymine (T). In the present specification, the "NNK sequence" refers to an oligonucleotide sequence containing a plurality of "NNK" (i.e., "NNK"×m (m is an integer of 2 or more)) successively. In the present specification, "NNS sequence" refers to an oligonucleotide sequence containing a plurality of "NNS" (i.e., "NNS"×m (m is an integer of 2 or more)) successively. In the present specification, "NNY sequence" refers to an oligonucleotide sequence containing a plurality of "NNY" (i.e., "NNY"×m (m is an integer of 2 or more)) successively. In one embodiment, the random oligonucleotide library is an oligonucleotide library containing repeats of NNK sequence, NNS sequence or NNY sequence. The "oligonucleotide library containing repeats of NNK sequence, NNS sequence or NNY sequence" refers to an oligonucleotide containing a plurality of random sequences selected from NNK sequence, NNS sequence and NNY sequence in one oligonucleotide. In this case, a plurality of NNK sequence, NNS sequence or NNY sequence may be contained, or a plurality of mutually different random sequences may be contained so that both NNK sequence and NNS sequence are contained. The oligonucleotide constituting the random oligonucleotide library in the present specification has, for example, 3×n bases. Examples of n include not less than 5 and not more than 20, and not less than 7 and not more than 11. A specific example of n is 9. A method for synthesizing a random nucleotide library is known. Therefore, a random nucleotide library may be produced by a known method.

In the above-mentioned method, the tag sequence to be added to the 5' terminus of the maturation target oligonucleotide library is exemplified by FLAG sequence. The tag sequence is not limited to FLAG sequence. Other example of the tag sequence is Myc sequence. An antibody that specifically binds to FLAG tag and Myc tag is already commercially available. Therefore, a protein fused with such tag can be easily labeled and purified using an antibody or a substance having an immobilized antibody. For example, when a ribosome display complex containing the maturated oligonucleotide library of the present invention has FLAG tag, the ribosome display complex can be easily recovered and purified using beads with an immobilized anti-FLAG antibody.

The arrest sequence is a sequence that stalls the translation on ribosome on the way. An arrest sequence derived from *Escherichia coli* is exemplified by SecM sequence (Nakatogawa and Ito (2002) Cell, vol. 108, p. 629-636) and TnaC sequence (Gong et al, (2002) Science, vol. 297, p. 1864-1867). In addition, an artificially synthesized arrest sequence for *Escherichia coli* is exemplified by the sequence reported by Tanner et al. (Tanner et al, (2009) J. Biol. Chem., vol. 284, p. 34809-34818). Furthermore, a eukaryote-derived arrest sequence is exemplified by uORF sequence (Hood et al, (2009) Annu. Rev. Microbiol, vol. 63, p. 385-409).

Then, a terminal-modified sequence product is transcribed to give a transcript. The transcription step is known in the field of biotechnology. Thus, the transcription step can be performed based on a known method.

Thereafter, the transcript is translated in vitro. This translation step is exemplified by translation of a transcript in vitro using a cell-free translation system. In this case, the maturation efficiency of oligonucleotide can be improved by performing the treatment completely in vitro. When a sequence derived from *Escherichia coli* is used as an arrest sequence, a preferable cell-free translation system is, for example, an *Escherichia coli* cell-free translation system. A preferable cell-free translation system is a reconstituted cell-free translation system, namely, PURE system (see, for example, "Shimizu Y, Inoue A, Tomari Y, Suzuki T, Yokogawa T, Nishikawa K, Ueda T (2001) Cell-free translation reconstituted with purified components. Nature Biotechnology 19, 751-755").

PURE system is a cell-free translation system reconstituted with independently prepared factors necessary for translation. PURE system is almost free of contamination with nuclease and protease that decrease efficiency of ribosome display. Therefore, higher selection efficiency has been reported by using PURE system than a cell-free translation system of a cell extract type (Villemagne et al, (2006) J. Immunol. Methods, vol. 313, p. 140-148). On the other hand, many organisms are provided with a means to bypass translation stalling on ribosome that occurs during translation. In the case of *Escherichia coli*, for example, a reaction called trans-translation involving 10S-RNA (tmRNA) and SmpB protein occurs, and ribosome stalling is cancelled (Moore and Sauer (2007) Annu. Rev. Biochem., vol. 76, p. 101-124). A general cell-free translation system of a cell-extract type containing an intracellular component also includes such bypass component in the system. Therefore, the formation efficiency of ribosome display complex is considered to decrease when a cell-free translation system of a cell-extract type is used. In fact, it has been reported that the formation efficiency of ribosome display complex increases by adding an antisense sequence of 10S-RNA to a cell-free translation system of an *Escherichia coli-extract* system (Hanes et al, (1997) Proc. Natl. Acad. Sci. USA, vol. 94, p. 4937-4942). That is, in the present invention, a PURE system free of the bypass component explained above is an optimal cell-free translation system.

A cell-free translation system has an energy regeneration system and at least one amino acid. Energy regeneration system means factors involved in the regeneration of energy sources necessary for protein synthesis such as ATP, GTP and the like. Examples of substances of the energy regeneration system include enzymes involved in ATP regeneration (creatinine kinase, pyruvate kinase etc.), and substrates thereof (phosphocreatine, phosphoenolpyruvate etc.). A cell-free translation system contains at least one kind of amino acid, preferably naturally-occurring 20 kinds of amino acids. A cell-free translation system may further contain a non-natural amino acid. A cell-free translation system may contain, for example, buffers (e.g., HEPES-potassium, Tris-acetate etc.), various salts, surfactants, RNA polymerases (T7, T3, and SP6 RNA polymerases etc.), chaperone proteins (DnaJ, DnaK, GroE, GroEL, GroES, and HSP70 etc.), RNA (mRNA, tRNA etc.), protease inhibitors, or (ribo)nuclease inhibitors.

As explained above, preferable use of the present invention is a method of maturation of a random oligonucleotide library using ribosome display. Ribosome display is a method that includes forming an mRNA-ribosome-oligopeptide ternary complex in in vitro translation system and selecting a protein encoding a polypeptide having a specific function. As mentioned above, the terminal-modified sequence product of the present invention has an arrest sequence at the 3' terminus of the maturation target oligonucleotide library. When an oligonucleotide constituting a random oligonucleotide library introduced into an in vitro translation system contains a stop codon, or when a frame shift exists due to the deletion or insertion of bases, normal translation up to the arrest sequence is not available during translation. Thus, translation of an oligonucleotide having a stop codon introduced therein or an oligonucleotide containing a frame shift fails to form a ternary complex of mRNA-ribosome-oligopeptide.

For example, only an in-frame oligonucleotide translated up to the arrest sequence can be selected by, for example, selecting such complex with an antibody to the introduced tag sequence.

The present invention is explained in more detail in the following by referring to Examples, which are not to be construed as limitative.

Example 1

Construction of Template

A maturation target random oligonucleotide library containing codons encoding 9 amino acids, which is added with a FLAG sequence at the 5' terminus and added with a Myc sequence at the 3' terminus, was prepared by DNA synthesis (SEQ ID NO: 1: ATGGACTATAAAGATGACGATGA-CAAAnnsnnsnnsnnsnnsnnsnnsnnsnnsGAGCAGAA GCT-GATCTCTGAGGAGGATCTG). A 5' UTR sequence comprising a T7 promoter and an SD sequence, which is added with a FLAG sequence at the 3' terminus, was also prepared by DNA synthesis (SEQ ID NO: 2: gaaattaatacgactcactatagg-gagaccacaacggtttccctctagaaataattttgttt aactttaagaag-gagatataccaatggactataaagatgacgatgacaaa). The partial sequence (220-326-position amino acid residues) of gene III of M13 phage was amplified by PCR with KOD Plus DNA Polymerase (manufactured by TOYOBO) (denaturation: 94° C., 15 seconds, annealing: 57° C., 30 seconds, extension: 68° C., 60 seconds, 25 cycles) using a phage genome derived from M13KO7 as a template and primer Myc-g3p (SEQ ID NO: 3: GAGCAGAAGCTGATCTCTGAGGAG-GATCTGGAATATCAAGGCCAATCGTCTGAC) and primer g3p-SecMstop (SEQ ID NO: 4: CTCGAGTTAT-TCATTAGGTGAGGCGTTGAGGGCCAG-CACGGATGCCTTGCGCCTGGCTTATC CAGACGGGCGTGCTGAATTTTGCGCCG-GAAACGTCACCAATGAAAC), and purified with a purification column manufactured by Qiagen. A PCR reaction solution containing the three kinds of DNAs (5' UTR, random oligonucleotide library and g3p, each 1 pmol), 5' primer (SEQ ID NO: 5: gaaattaatacgactcactatagg-gagaccacaacggtttccctctag) (10 pmol), SecM stop sequence (SEQ ID NO: 6: ggattagttattcattaggtgaggcgttgagg) (10 pmol) and KOD Plus DNA polymerase was prepared, and subjected to 10 cycles of PCR reaction (denaturation: 94° C., 15 seconds, annealing: 57° C., 30 seconds, extension: 68° C., 60 seconds). After confirmation of a band containing three genes linked together by electrophoresis using 1% agarose gel, the band was excised and purified with a column manufactured by Qiagen to finally give a maturation target oligonucleotide library containing the random sequence.

In Vitro Transcription

The purified maturation target oligonucleotide library DNA (1 μg) was transcribed into mRNA with 20 μl of in vitro transcription kit (Ribomax™ Large Scale RNA Production System-T7, Promega), and purified with a column (RNeasy mini column, Qiagen).

In vitro translation using a cell-free translation system (construction of ribosome-Peptide-mRNA complex): a cell-free translation system (PURE system), which is a protein synthesis reaction reagent, was prepared according to the previous report (Shimizu et al. (2005) Methods, vol. 36, p. 299-304). To the prepared reaction solution (100 μl) was added maturation target oligonucleotide library mRNA (100 pmol), and the mixture was incubated at 37° C. for 30 min. An ice-cooled Wash buffer (50 mM Tris-OAc, pH 7.5, 150 mM NaCl, 50 mM Mg(OAc)$_2$, 0.5% Tween 20, 10 μg/ml budding yeast (*Saccharomyces cereviseae*) total RNA (manufactured by Sigma)) (500 μL), a Blocking buffer (50 mM Tris-OAc, pH 7.5, 150 mM NaCl, 50 mM Mg(OAc)$_2$, 0.5% Tween 20, 10 μg/ml budding yeast (*Saccharomyces cereviseae*) total RNA (manufactured by Sigma), and 5% SuperBlock (Pierce)) (500 μL) were added.

In Vitro Selection

A FLAG M2 carrier (50 μL slurry, manufactured by Sigma) which was blocked with 5% SuperBlock at 4° C. overnight in advance was washed twice with 500 μl of Wash buffer using MicroSpin (registered trade mark) column (manufactured by GE Healthcare), after which translation reaction solution was added to the recovered FLAG M2 carrier, and the mixture was stirred by rotation at 4° C. for 1 hr. The supernatant was discarded using MicroSpin (registered trademark) column (manufactured by GE Healthcare); 1 mL of Wash buffer was added to the recovered FLAG M2 carrier, and stirred by rotation at 4° C. for 5 min. After this process was repeated 20 times, 100 μl of Elution buffer (50 mM Tris-OAc, pH 7.5, 150 mM NaCl, 50 μg of FLAG peptide (Sigma)) was added to the recovered FLAG M2 carrier, and the mixture was allowed to stand at 4° C. for 15 minutes. Thus, the complex was separated from the FLAG M2 carrier. The supernatant was recovered with MicroSpin (registered trade mark) column (manufactured by GE Healthcare), and mRNA was recovered and purified with RNeasy Micro (manufactured by Qiagen).

RT-PCR

The recovered mRNA was processed into cDNA with Transcription High Fidelity cDNA Synthesis Kit (Roche), and subjected to a PCR reaction using KOD Plus DNA polymerase (denaturation: 94° C., 15 seconds; annealing: 57° C., 30 seconds; extension: 68° C., 60 seconds; 20 cycles). The primers used are shown below.

```
reverse transcription reverse primer:
Myc-R (SEQ ID NO: 7:
CAGATCCTCCTCAGAGATCAGC)

PCR primer:
FLAG-F (SEQ ID NO: 8:
atggactataaagatgacgatgacaaa)

Myc-R (SEQ ID NO: 7:
CAGATCCTCCTCAGAGATCAGC)
```

Subcloning for DNA Sequence Analysis

DNA (100 ng) before and after selection were added with A at the 3' terminus with rTaq DNA polymerase (manufactured by TOYOBO). Thereafter, subcloning was performed using a TOPO TA cloning kit (manufactured by Invitrogen). The subcloning was performed based on the explanation of this kit. *Escherichia coli* single colony after transformation (each 20 colonies) was cultured in 3 ml of LB medium, and plasmid was recovered from the amplified *Escherichia coli* and used for DNA sequence analysis.

Results and Discussion

FIG. 1 shows random oligonucleotide library (NNS sequence) before and after maturation.

As shown in FIG. 1, as a result of the DNA sequence analysis before maturation, the appearance frequency of oligonucleotide containing stop codon (TAG) was 40% (8/20), deletion of base was 5% (1/20), insertion of base was 0% (0/20), and the appearance frequency of finally complete in-frame oligonucleotide was 55% (11/20). In addition, after maturation, appearance frequency of those containing stop codon, and deletion and insertion of bases was 0% (0/20), and all oligonucleotides were confirmed to be in-frame. These results show that the selection of in-frame oligonucleotide has been almost completely achieved by the present method, and the effectiveness of the present method has been verified.

[Sequence Listing Free Text]

SEQ ID NO: 1: oligonucleotide n shows optional base.

s shows guanine or cytosine.

SEQ ID NO: 2: oligonucleotide comprising T7 promoter, SD sequence and initiation codon SEQ ID NOs: 3-8: primer

INDUSTRIAL APPLICABILITY

The production method of a maturated oligonucleotide library of the present invention can be utilized in, for example, biochemical industry and protein drug industry.

This application is based on a patent application No. 2010-142470 filed in Japan (filing date: Jun. 23, 2010), the contents of which are incorporated in full herein.

The invention claimed is:

1. A method of producing a maturated oligonucleotide library, comprising
providing a maturation target oligonucleotide library,
adding (i) a tag sequence to the 5' terminus of the maturation target oligonucleotide library and (ii) an arrest sequence, which stalls translation elongation on a ribosome, to the 3' terminus of the maturation target oligonucleotide library to obtain a terminal-modified product of a maturation target oligonucleotide library,
transcribing the terminal-modified sequence product to yield a transcript,
performing an in vitro translation step to translate the transcript in vitro to yield an mRNA-ribosome-oligopeptide ternary complex comprising a translated tag sequence, and
selecting the complex with an antibody to the translated tag sequence,
wherein the maturation target oligonucleotide library is an oligonucleotide library containing NNK sequence, NNS sequence, or NNY sequence, or an oligonucleotide library containing NNN sequences.

2. The method of claim 1, wherein the arrest sequence is SecM sequence.

3. The method of claim 1, wherein the tag sequence is FLAG sequence.

4. The method of claim 1, wherein the in vitro translation uses a cell-free translation system.

5. The method of claim 1, wherein the in vitro translation uses an *Escherichia coli* cell-free translation system.

6. The method of claim 1, wherein the in vitro translation uses a reconstituted cell-free translation system.

7. The method of claim 2, wherein the tag sequence is FLAG sequence.

8. The method of claim 7, wherein the in vitro translation uses a cell-free translation system.

9. The method of claim 8, wherein the in vitro translation uses an *Escherichia coli* cell-free translation system.

10. The method of claim 8, wherein the in vitro translation uses a reconstituted cell-free translation system.

* * * * *

UNITED STATES PATENT AND TRADEMARK OFFICE
CERTIFICATE OF CORRECTION

PATENT NO. : 9,133,452 B2  
APPLICATION NO. : 13/806470  
DATED : September 15, 2015  
INVENTOR(S) : Ueda et al.

Page 1 of 1

It is certified that error appears in the above-identified patent and that said Letters Patent is hereby corrected as shown below:

On the title page:

(87) PCT Pub. No.: WO2001/162355 should read

(87) PCT Pub. No.: WO2011/162355

Signed and Sealed this
Twenty-second Day of March, 2016

Michelle K. Lee
*Director of the United States Patent and Trademark Office*